United States Patent [19]

Zimmer

[11] 3,948,269
[45] Apr. 6, 1976

[54] CRYOMEDICAL DEVICE

[75] Inventor: Hildebrand Zimmer, Ahrensbrug, Germany

[73] Assignee: Dragerwerk Aktiengesellschaft, Germany

[22] Filed: Aug. 29, 1974

[21] Appl. No.: 501,766

[30] Foreign Application Priority Data
Aug. 31, 1973 Germany............................ 2343910

[52] U.S. Cl. ............................................. 128/303.1
[51] Int. Cl.² ......................................... A61B 17/36
[58] Field of Search .......... 128/303.1, 399, 400, 401

[56] References Cited
UNITED STATES PATENTS

| | | | |
|---|---|---|---|
| 3,272,203 | 9/1966 | Chato | 128/303.1 |
| 3,298,371 | 1/1967 | Lee | 128/303.1 |
| 3,421,508 | 1/1969 | Nestrock | 128/303.1 |
| 3,782,386 | 1/1974 | Barger et al. | 128/303.1 |
| 3,789,853 | 2/1974 | Reinhard | 128/399 |

*Primary Examiner*—Channing L. Pace
*Attorney, Agent, or Firm*—McGlew and Tuttle

[57] ABSTRACT

A cryomedical device, comprises a probe which is adapted to be positioned to rapidly cool a body portion of a patient, and which is connected to a coolant supply which supplies coolant thereto at a predetermined rate. Means are provided for sensing the temperature in the vicinity of the probe, for example, a thermocouple element in the probe itself or a needle which may be injected into the body, and one, or both of these are connected to a control for regulating the supply of coolant. In addition, a heater may be provided in the probe and the control may be connected to regulate the heater. In the preferred arrangement, the control includes a device for setting the temperature value of operation which is connected to a comparator to provide a control between the set value and the actual value of the temperature of the body in the vicinity of the probe.

7 Claims, 1 Drawing Figure

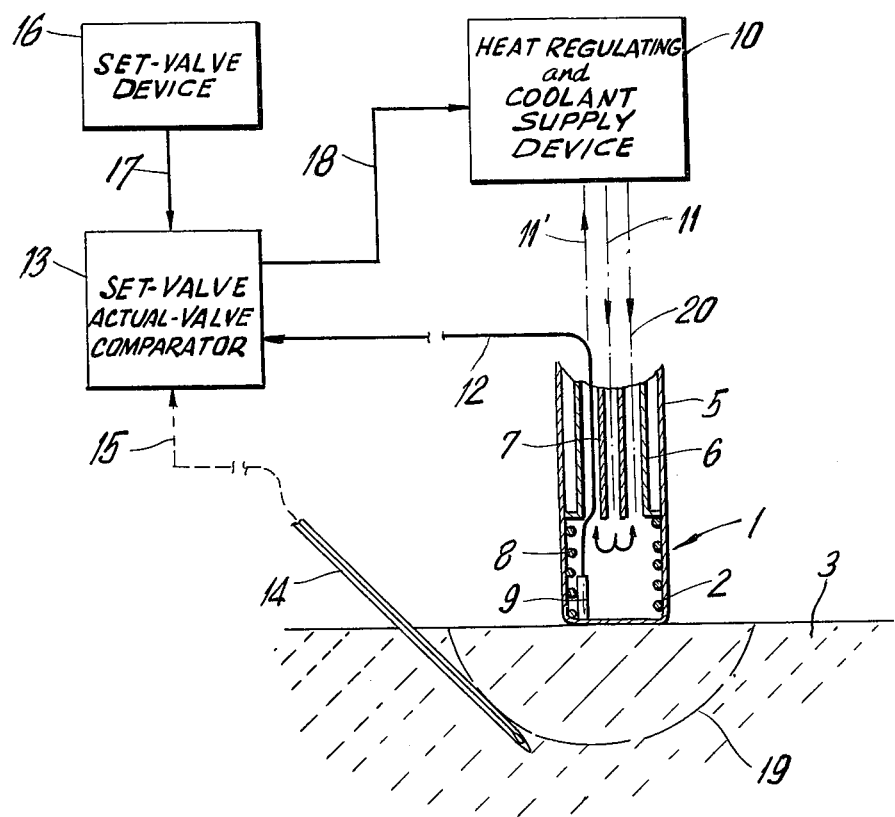

CRYOMEDICAL DEVICE

BACKGROUND OF THE INVENTION

1. Field of the Invention

This invention relates in general to the construction of devices for cooling body parts and, in particular, to a new and useful cryomedical device which includes a probe having means for cooling it to very low temperatures and with means for controlling the temperatures in accordance with the body treatment which is to be effected.

2. Description of the Prior Art

Cryomedical probes are known wherein refrigerating agents or coolants are supplied from a supply to the probe through a flexible tube. The supply apparatus also serves to supply current to a heating member which is located adjacent the contact surface of the probe in order to reheat this surface after a cooling operation.

SUMMARY OF THE INVENTION

The present invention provides a cryomedical device which includes a probe which is refrigerable to a low temperature and which is connected to a coolant supply apparatus which is adjusted so that the coolant may be supplied at a rate in accordance with the actual conditions of the body during the treatment. The supply is such that it can be regulated so that the temperature of the probe can be adjusted to predeterminable constant temperatures and also to temperatures varying over a time period in a predetermined manner (dT/dt).

In accordance with the invention, the supply apparatus for the coolant is connected with means for controlling the temperature programs for the probe. A cryomedical device designed in this manner makes it possible, for example, to kill biological tissues or swollen areas of the body or similar conditions in a particularly simple manner by refrigeration. To this end, the biological tissue to be killed is subjected to a rapid freezing and a slow thawing operation. The particular advantage of the invention is that the freezing operation and the thawing of the biological tissues can be carried out in a reproducible or automatic manner.

The temperature controlling means comprises a set value element, an actual value element and a set value-/actual value comparator. In order to obtain the actual value of the temperature, a thermocouple located at the probe or a thermoneedle which is stuck into the tissue in the zone or location of the treatment may be provided for single or joint operation. In the case of the thermocouple, it is set to emit voltage signals which correspond to the actual temperatures, and it can be connected without difficulties to an electronic control means for regulating the set value/actual value comparator. The use of the thermoneedle has the advantage that the actual temperature value at the location of the tissue may be determined and at the depth of penetration which may be determined by the attending physician. Thereby, an undesired freezing of any sound tissue can be avoided in a simple manner.

Accordingly, it is an object of the invention to provide a cryomedical device which comprises a probe which is adapted to be positioned to rapidly cool a body part and which is connected to a coolant supply means which is regulatable to supply a coolant thereto to effect a controlled cooling and subsequent thawing of the body tissue and which also includes means for sensing the temperature in the vicinity of the probe which is connected to control means for regulating the coolant supply to effect a desired controlled probe temperature.

A further object of the invention is to provide a cryoprobe or cryomedical device which is simple in design, rugged in construction, and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there is illustrated a preferred embodiment of the invention.

BRIEF DESCRIPTION OF THE DRAWING

The only FIGURE of the drawing is a transverse sectional view of a cryomedical probe with a schematic representation of the control elements connected thereto for regulating the temperature thereof.

DESCRIPTION OF THE PREFERRED EMBODIMENT

Referring to the drawing in particular, the invention embodied therein comprises a cryomedical device which includes a cryoprobe 1, of which only a small portion is shown. Cryoprobe 1 includes a front end 2 which, during treatment, is brought into contact with a body portion or tissue 3. Probe 1 includes an evaporation chamber 4 in a shaft portion 5 located at the end adjacent a contact surface 5a which is in engagement with the tissue 3. At least a portion of the shaft 5 is of double-walled construction and includes a vacuum jacket 6 for thermal insulation. A central coolant supply tube 7 for the cooling agent, such as a liquid nitrogen, is connected to a coolant supply device 10 and terminates in an opening at the evaporation chamber 4. The space around the exterior of the supply tube 7 forms a return conduit for the coolant which leads from the evaporation chamber 4 to the coolant supply device, via supply and return conduits 11 and 11'. A resistance heater 8 is arranged at the periphery of the evaporation chamber 4 and is connected through an electrical connection 20 to a heat regulating element in the heat regulating and coolant supply device 10.

In accordance with a feature of the invention, temperature sensing means are associated with probe 1 and it includes either a thermocouple 9 located within shaft 5 which is connected through a connecting cable 12 to a set value/actual value comparator 13 or a thermoneedle 14 which may be injected into skin 3. Thermoneedle 14 is connected through a connecting cable 15 to the set value/actual value comparator 13.

Both the coolant agent supply through tube 7 and the heating effect of the heating wire 8 are controlled by the heat regulating and coolant supply device 10. The voltage signal furnished by the thermocouple 9 passes as an actual value through line 12 to the set value/actual value comparator 13. The actual value temperature may also be measured by the thermoneedle 14 and furnished to the set value/actual value comparator 13 through the connecting line 15.

A set value device 16 is such that any temperature program can be adjusted for carrying out the freezing operations and it is connected through the line 17 to the set value/actual value comparator 13. The combined control means 13 and 16 permit a programmed control of both cooling and heating supplied through the heat regulating and coolant supply device 10. In operation, therefore, for example, a rapid freezing and a slow thawing may be obtained as desired. The voltage signal corresponding to the set value passes to the set value/actual value comparator through the line 17. Line 18 connects the set value/actual value comparator 13 to the heat regulating and coolant supply device 10, so that the supply of coolant and the return of the coolant is regulated or the amount of heating of heater 8 is controlled as desired. If, for example, the portion of the tissue designated 19 is to be killed, to which end a rapid freezing of this portion and a slow thawing is necessary, first the thermoneedle is stuck into the tissue so that its point comes into the position immediately beneath the portion of the tissue to be killed. Thereupon, the set value element is adjusted so as to obtain the most rapid possible cooling of the probe and thereby, of the tissue, and the freezing operation is carried out until the ice ball which will be formed has a desired size and, for example, until the temperature of the point of the thermoneedle drops to 0°C. The speed of the subsequent thawing operation is also adjustable by means of the set value element 16 so that the stopping of the cooling agent supply and the intensification of the heating of the heater 8 will be automatically controlled.

The particular advantage of the refrigeration treatment using the device designed in accordance with the invention is that the treatment procedure may be reproduced and repeated and the conditions under which certain refrigeration treatments is carried out may be recorded and, if particularly successful, the treatment conditions may be repeated under exactly the same conditions.

While a specific embodiment of the invention has been shown and described in detail to illustrate the application of the principles of the invention, it will be understood that the invention may be embodied otherwise without departing from such principles.

What is claimed is:

1. A cryomedical device for use in freezing the tissue of a body part, comprising a probe which is adapted to be positioned adjacent the body part for the rapid cooling of the tissue thereof, coolant supply means connected to said probe for supplying coolant at a selected rate thereto, first temperature sensing means in said probe adjacent the contact surface for sensing the probe temperature, second temperature sensing means for sensing the affected tissue temperature including a needle having means for penetrating the tissue for sensing the temperature below the surface of the tissue and control means connected to said first and second temperature sensing means and said coolant supply means for regulating the supply of coolant to said probe to control the temperature thereof in accordance with the temperature of the tissue.

2. A cryomedical device, according to claim 1, wherein said first temperature sensing means comprises a thermocouple located adjacent the contacting end of said probe.

3. A cryomedical device, according to claim 1, wherein said probe has a heater, said coolant supply means including means for regulating said heater in addition to regulating the supply of coolant.

4. A cryomedical device comprising a tubular probe having an end terminating in a surface adapted to contact a body tissue, an electrical resistance heater in said probe adjacent the surface adapted to contact the tissue, the interior of said probe adjacent the probe contact surface defining an evaporation chamber for a coolant, supply conduit means for the supply and return of coolant, a heat regulating and coolant supply device connected to said heater and to said coolant supply and return conduits for regulatng the supply of coolant and the amount of heating of said heater, first temperature sensing means in said probe adjacent the contact surface for sensing the probe temperature, second temperature sensing means for sensing the affected tissue temperature including a needle having means for sensing the temperature adapted to penetrate the tissue, control means connected to said first and second temperature sensing means and to said heat regulating and coolant supply device and to said heater for regulating the amount of coolant supplied over a predetermined time and the amount of heating carried out in a period of time in accordance with the temperature of the tissue.

5. A cryomedical device, according to claim 4, wherein said control means includes a set value device for setting a particular value of temperature operation, said thermocouple and said needle being connected to said control for establishing an actual value and including a set value and actual value comparator for comparing the actual and set values and for regulating the heat and coolant supply accordingly.

6. A method of treating a tissue using a probe which is adapted to be positioned adjacent the body part and supplied with a coolant for the freezing of the body part tissue and a penetrating needle having means for sensing temperature at its penetrating point, comprising supplying a coolant to the probe and contacting the tissue with the probe to rapidly cool the tissue, inserting a needle into the tissue up to the area at which the tissue is to be frozen, and sensing the temperature at the area during the cooling of the tissue with the probe, and regulating the amount of coolant delivered to the probe in accordance with the temperature sensed by the needle.

7. A method according to claim 6, including supplying heat to the probe in order to rapidly heat it to discontinue its cooling operation when the temperature at the needle is sensed as being close to the desired freezing temperature.

* * * * *